United States Patent
Blanchard et al.

(10) Patent No.: US 6,995,838 B2
(45) Date of Patent: Feb. 7, 2006

(54) DEVICE FOR AUTOMATIC SURFACE INSPECTION OF AN UNWINDING STRIP

(75) Inventors: Dominique Blanchard, Metz (FR); Stéphane Auger, Le Ban Saint Martin (FR)

(73) Assignee: Usinor, Puteaux (FR)

( * ) Notice: Subject to any disclaimer, the term of this patent is extended or adjusted under 35 U.S.C. 154(b) by 0 days.

(21) Appl. No.: 10/415,421

(22) PCT Filed: Dec. 10, 2001

(86) PCT No.: PCT/FR01/03904

§ 371 (c)(1),
(2), (4) Date: Apr. 29, 2003

(87) PCT Pub. No.: WO02/48695

PCT Pub. Date: Jun. 20, 2002

(65) Prior Publication Data

US 2004/0021857 A1     Feb. 5, 2004

(30) Foreign Application Priority Data

Dec. 11, 2000  (FR) .................................. 00 16093

(51) Int. Cl.
G01N 21/00 (2006.01)
G01N 21/84 (2006.01)
(52) U.S. Cl. .................................. 356/237.2; 356/430
(58) Field of Classification Search .. 356/237.1–237.3, 356/429–431
See application file for complete search history.

(56) References Cited

U.S. PATENT DOCUMENTS

| | | | |
|---|---|---|---|
| 5,153,844 A | * | 10/1992 | Beni et al. ................... 702/167 |
| 5,897,195 A | | 4/1999 | Choate |
| 2002/0018201 A1 | * | 2/2002 | Young et al. ............ 356/239.2 |
| 2002/0154308 A1 | * | 10/2002 | Uesugi et al. .............. 356/431 |

FOREIGN PATENT DOCUMENTS

WO  WO00/55605   * 9/2000
WO  WO 00 66999     11/2000

OTHER PUBLICATIONS

Patent Abstracts of Japan, vol. 013, No. 353 (P-913), Aug. 8, 1989 & JP 01 113639 (Furukawa Electric Co., LTD.), Dec. 26, 1987.
Patent Abstracts of Japan, vol. 012, No. 194 (P-713), Jun. 7, 1988 & JP 62 299749 (Furukawa Electric Co., Ltd.), Dec. 26, 1987.
Patent Abstracts of Japan, vol. 2000, No. 04, Aug. 31, 2000 & JP 2000 028341 (Nissan Motor Co., Ltd.), Jan. 28, 2000.

* cited by examiner

*Primary Examiner*—Michael P. Stafira
(74) *Attorney, Agent, or Firm*—Sughrue Mion, PLLC

(57) ABSTRACT

The invention concerns a device for automatic surface inspection of an unwinding strip to detect surface defects, comprising at least a camera (10) whereof the optical axis is directed towards the surface to be inspected and forming on said surface a transverse line of sight (L) and at least an illuminating system (15) whereof the incident rays (Ri) are directed towards the transverse tranline of sight and distributed over the entire length of said line. At each point of the transverse line of sight, the observation direction of the camera (10) forms with the specular reflected ray at said point a constant angle.

6 Claims, 2 Drawing Sheets

DEVICE FOR AUTOMATIC SURFACE INSPECTION OF AN UNWINDING STRIP

BACKGROUND OF THE INVENTION

The present invention relates to a process for the automatic surface inspection of a moving strip, in particular a sheet of rolled metal, or of plates moving past at high speed, in order to detect surface defects.

A first conventional technique for the surface inspection of a strip consists in carrying out a visual check of the surface of the strip.

Such a technique has disadvantages owing to the fact that it is very constraining for the operator, and subjective, and does not ensure constancy of inspection of the strips.

In addition, it makes it necessary to cause the strip to pass via a specific line operating at reduced speed, which has a detrimental effect on the efficiency of manufacture of the strips.

Another known technique of surface inspection consists in checking the surface state of the strip automatically by means of, on the one hand, a camera whose optical axis is directed towards the surface to be inspected and which forms on the said surface a line of sight which is transverse relative to the direction of movement of the strip and, on the other hand, a lighting system illuminating the width of the strip at the location of the line of sight, and finally a signal-processing unit for the real-time analysis of the images supplied by the camera.

Conventional lighting systems of automatic surface inspection devices produce lighting whose emitted rays are, in the transverse direction, perpendicular to the strip. The result is that, at each point of the transverse line of sight, the direction of observation of the camera forms a variable angle with the specular reflected ray.

However, with this kind of lighting system, some types of defect are difficult to detect or are not detected. This is the case in particular of long mechanical defects in the direction of rolling.

In order to improve the detection of this type of defect, one solution consists in providing lighting whose rays are no longer emitted perpendicularly to the strip.

For that purpose, there are systems capable of producing this type of lighting whose principal angle of ray emission is constant in the direction perpendicular to the direction of movement of the strip.

However, the application of these systems has two major disadvantages. On the one hand, the visibility of a given defect is not constant as a function of the position of this defect along the line of sight and, on the other hand, the signal recorded by the camera and constituting the image of the strip exhibits variations in amplitude in the transverse direction.

These disadvantages are a real obstacle to efficient exploitation of the images obtained by means of such light sources.

SUMMARY OF THE INVENTION

The object of the invention is to avoid these disadvantages by proposing an automatic inspection device which permits a significant increase in the visibility of defects and the obtaining of a constant signal in the transverse direction recorded by a camera, thus improving the detection of these defects.

The invention therefore relates to a device for the automatic surface inspection of a moving strip, in order to detect surface defects, of the type comprising, on the one hand, at least one camera whose optical axis is directed towards the surface to be inspected and which forms with the said surface a line of sight which is transverse relative to the direction of movement of the strip and, on the other hand, at least one lighting system whose incident rays are directed towards the transverse line of sight and are distributed over the entire length of the said line, characterised in that, at the location of each point of the transverse line of sight, the direction of observation of the camera forms a constant angle with the specular reflected ray at the said point.

According to other features of the invention:
- the specular reflected ray on the line of sight forms with the perpendicular to the surface to be inspected an angle whose value varies continuously along the line of sight, its minimum value corresponding to the centre of the line of sight and its maximum value to the end of the line of sight,
- the lighting system is formed by at least one row of optical fibres,
- the lighting system is formed by at least one row of light-emitting diodes,
- the lighting system is formed by a linear light source associated with at least one optical element for directing the incident rays towards the transverse line of sight,
- the camera is inclined, relative to an axis which is perpendicular to the surface to be inspected and which extends through the point of intersection of the optical axis of the camera on the said surface, by an angle of from 0 to 70°.

BRIEF DESCRIPTION OF THE DRAWING

Other features and advantages of the invention will emerge on reading the following description which is given by way of example and with reference to the appended drawings, in which.

DETAILED DESCRIPTION OF THE INVENTION

Figure 1:
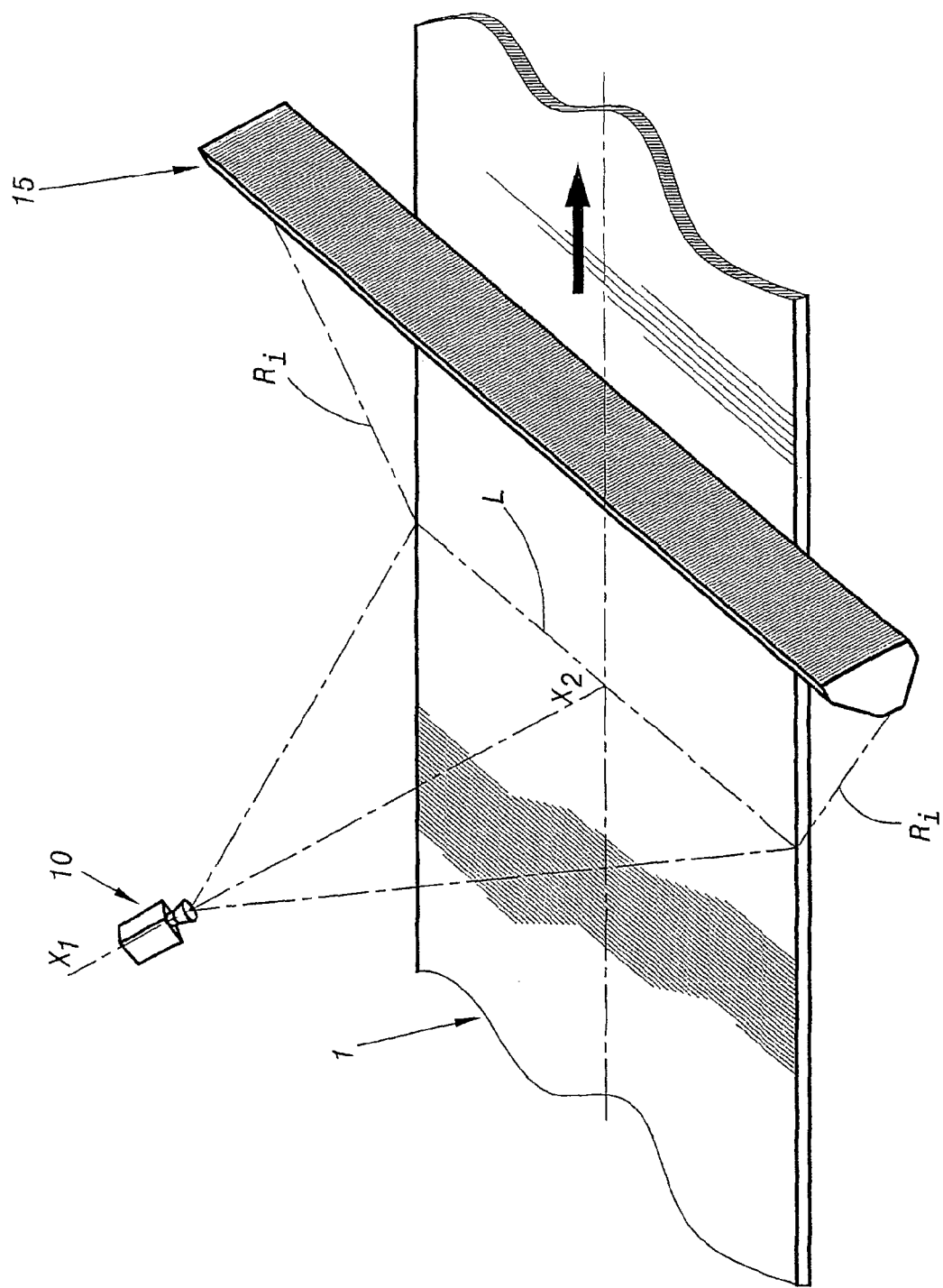
FIG. 1 is a diagrammatic perspective view of a device for the surface inspection of a moving strip, according to the invention.

The device shown in FIG. 1 is for inspecting a surface of a strip 1 as it moves past at high speed, for example, a rolled strip emerging from a rolling line, in order to detect surface defects.

Each surface of the strip 1 is inspected by means of a camera 10 whose optical axis $X_1 X_2$ is directed towards the surface to be inspected.

In the embodiment shown, the device comprises a single camera 10 directed onto one of the surfaces of the strip 1, but the device may of course be equipped with two cameras suitable for forming images of each surface of the strip 1.

The camera 10 may be constituted by any type of apparatus suitable for the intended use, such as, for example, a camera forming on the surface of the strip 1 a line of sight L which is transverse relative to the direction of movement of the strip 1.

In the embodiment shown in the Figures, the breadth of field of the camera 10 is equal to or slightly larger than the width of the inspection region of the strip 1.

Thus, the transverse line of sight L is equal to or slightly larger than the width of the strip 1.

In a case where one camera is not sufficient to cover all of the width of the strip 1, several cameras distributed over the width of the strip 1 are used.

The camera 10 acquires the image of the surface of the strip 1 as the latter moves past and, in order to improve the visibility of any defects on this surface to be inspected, such as, for example, scores or scratches, the inspection device also comprises at least one lighting system, such as strip-form lighting 15.

As shown in FIG. 1, the incident rays $R_i$ are directed towards the transverse line of sight L and are distributed over the entire length of this line of sight.

Figure 2:
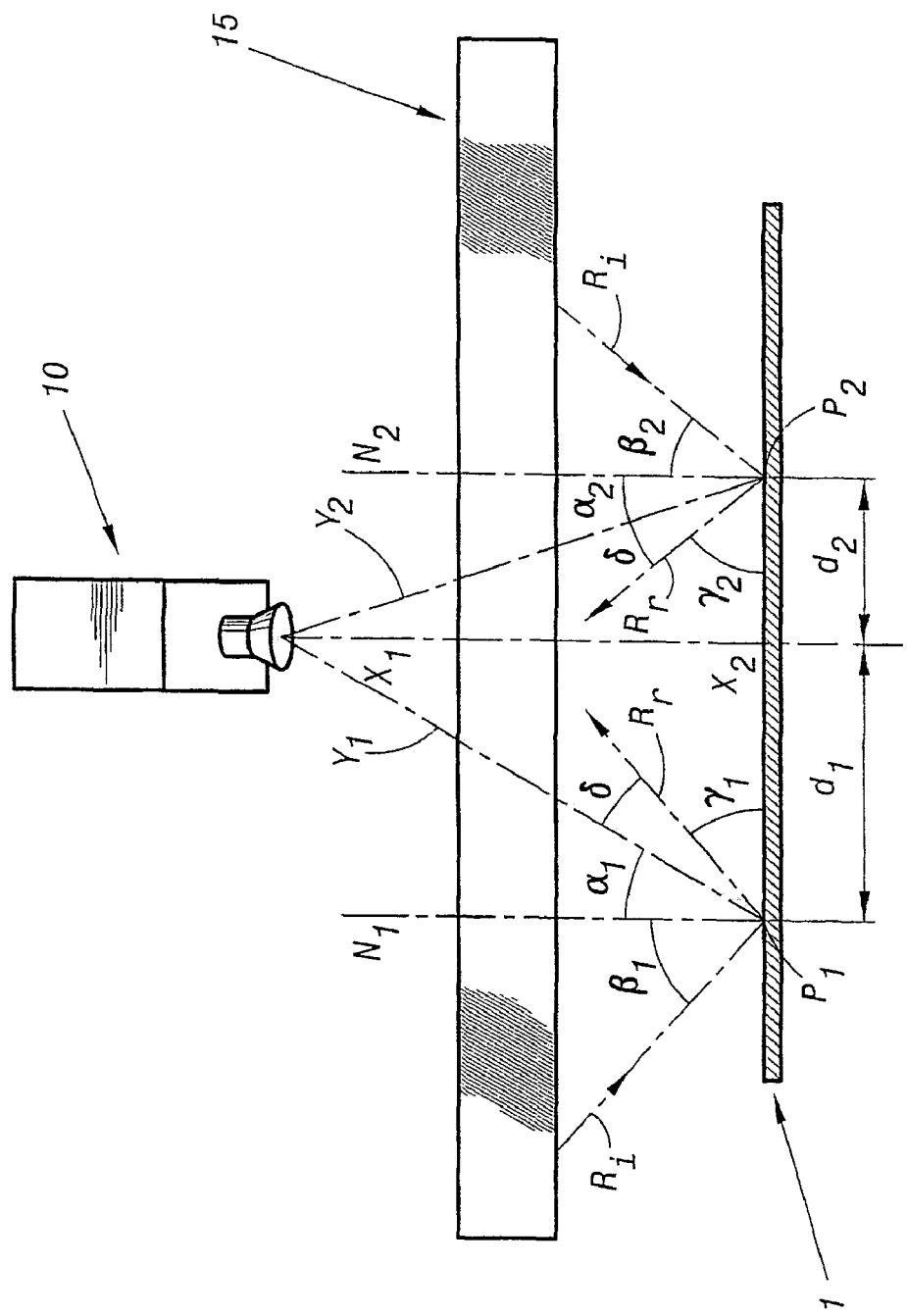
FIG. 2 is a diagrammatic view showing the optical configuration of the inspection device according to the invention.

As shown in FIG. 2, the lighting system 15 is designed in such a manner that, at the location of each point of the transverse line of sight L, the direction of observation y of the camera 10 forms a constant angle d with the specular reflected ray $R_r$ at the said point.

The specular reflected ray $R_r$ is the reflected ray that forms with a perpendicular to the point of impact on the surface of the strip 1, an angle which is equal to the angle formed by the incident ray $R_i$ with this perpendicular at the said point.

In FIG. 2, two points $P_1$ and $P_2$, respectively, have been selected by way of example, these points being located on the transverse line of sight L and one on each side of the optical axis $X_1 X_2$ of the camera 10.

Thus, the point $P_1$ is at a distance $d_1$ from the optical axis $X_1 X_2$ of the camera 10 and the point $P_2$ is at a distance $d_2$ from the optical axis which is less than the distance $d_1$.

The incident ray $R_i$ emitted by the light source 15 to point $P_1$ forms an angle $b_1$ with the perpendicular $N_1$ to the surface of the strip 1 at the location of point $P_1$ and the direction of observation $Y_1$ of the camera 10 forms an angle $a_1$ with the perpendicular $N_1$ at point $P_1$. The specular reflected ray $R_r$ at point $P_1$ forms an angle d with the direction of observation $Y_1$ at point $P_1$.

Likewise, the incident ray $R_i$ emitted by the light source 15 forms at point $P_2$ with the perpendicular $N_2$ at the location of this point $P_2$ an angle $b_2$ and the direction of observation $Y_2$ of the camera 10 forms with the perpendicular $N_2$ at point $P_2$ an angle $a_2$. The specular reflected ray $R_r$ forms with the direction of observation $Y_2$ at point $P_2$, an angle d equal to the angle d formed with the specular reflected ray $R_r$ and the direction of observation $Y_1$ of the camera 10 at the location of point $P_1$.

Thus, in order to provide constant inspection conditions in the transverse direction, the incident rays form with a perpendicular at the location of each point of the transverse line of sight, an angle which varies continuously along the light source. The direction of observation $Y_x$ of the camera 10 forms, at each point of the transverse line of sight L, with the specular reflected ray at the location of each of the points, an angle which observes the relationship:

$$b_x - a_x = d_{constant}$$

Moreover, the specular reflected ray $R_r$, and of course the incident ray $R_i$, at a point taken on the line of sight L, form an angle c whose value varies continuously along the said line. The maximum value of this angle is situated at the centre of the line of sight L and its minimum value at the end of the line of sight.

By way of example, in the case of one camera 10 located on the longitudinal axis of the strip 1, as shown in the Figures, the angle of the specular reflected ray $R_r$ or of the incident ray $R_i$ varies on the line of sight L from 30 to 60°, this applying to each half-strip between a point located at the edge and a point located on the optical axis $X_1 X_2$ of the camera 10.

In the case of two cameras 10, each located on the longitudinal axis of a half-strip, the angle of the specular reflected ray $R_r$ or of the incident ray $R_i$ varies from 15° to 30°, this applying to each quarter of a strip.

The lighting system 15 is formed by at least one row of optical fibres or by at least one row of light-emitting diodes in such a manner as to be able to incline the incident ray in accordance with an angle determined as a function of the point of the transverse line of sight onto which the incident ray is directed.

According to a further variant, the lighting system 15 is formed by a linear light source associated with at least one optical element for directing the incident rays towards the transverse line of sight and for giving those incident rays the inclination that is desired as a function of the point located on the transverse line of sight.

The camera 10 is inclined, relative to an axis which is perpendicular to the inspection surface of the strip 1 and which extends through the point of intersection of the optical axis $X_1 X_2$ of the camera on the said surface, by an angle of from 0 to 70°.

The inspection device according to the invention using a lighting system illuminating the inspection surface of the strip on the side relative to the direction of movement of the strip permits a significant increase in the visibility of some types of defect, such as, for example, long mechanical defects in the direction of rolling.

Furthermore, this device makes it possible to obtain maximum and constant visibility of the defects over the entire width of a strip, such as, for example, a moving strip two metres wide, regardless of the position of the defect on the strip.

Therefore, the reliability of checks on the quality of the strips is increased, thus permitting rapid intervention during the process of manufacturing the strip in order to correct these defects as soon as possible and in order to avoid significant wastage.

The invention claimed is:

1. Device for the automatic surface inspection of a moving strip (1), in order to detect surface defects, of the type comprising, on the one hand, at least one camera (10) whose optical axis is directed towards the surface to be inspected and which forms with said surface a line of sight which is transverse relative to the direction of movement of the strip (1) and, on the other hand, at least one lighting system (15) whose incident rays are directed towards the transverse line of sight and are distributed over the entire length of said line, characterised in that the incident rays form, with a perpendicular at the location of each point of the transverse line of sight, an angle $\beta_x$ which varies continuously along the light source, and in that, at the location of each point of the transverse line of sight, the direction of observation of the camera (10) forms, with the specular reflected ray at said point, a constant angle $\delta$, and, with the perpendicular at the location of each of the points, an angle $\alpha_x$ which observes the relationship:

$$\beta x - \alpha x = \delta \text{constant}.$$

2. Inspection device according to claim 1, characterised in that the specular reflected ray on the line of sight forms with the perpendicular to the surface to be inspected an angle whose value varies continuously along the line of sight, its minimum value corresponding to the centre of the line of sight and its maximum value to the end of the line of sight.

3. Inspection device according to claim 1, characterised in that the lighting system (15) is formed by at least one row of optical fibres.

4. Inspection device according to claim 1, characterised in that the lighting system (15) is formed by at least one row of light-emitting diodes.

5. Inspection device according to claim 1, characterised in that the lighting system (15) is formed by a linear light source associated with an optical element for directing the incident rays towards the transverse line of sight.

6. Inspection device according to claim 1, characterised in that the camera (10) is inclined, relative to an axis which is perpendicular to the inspection surface of the strip (1) and which extends through the point of intersection of the optical axis of the camera on said surface, by an angle of from 0 to 70°.

* * * * *